United States Patent [19]
Negus et al.

[11] Patent Number: 5,617,258
[45] Date of Patent: Apr. 1, 1997

[54] NON-REUSABLE LENS CELL FOR A SURGICAL LASER HANDPIECE

[75] Inventors: Charles C. Negus; Stephen J. Linhares, both of Taunton, Mass.

[73] Assignee: PLC Medical Systems, Inc., Franklin, Mass.

[21] Appl. No.: 548,270

[22] Filed: Oct. 25, 1995

[51] Int. Cl.$^6$ ............................................. G02B 7/02
[52] U.S. Cl. ............................................. 359/819
[58] Field of Search ........................ 359/801, 803, 359/805, 806, 809, 811, 812, 818, 819

[56] References Cited

U.S. PATENT DOCUMENTS

| | | | |
|---|---|---|---|
| 4,431,267 | 2/1984 | Finck | 359/819 |
| 4,541,689 | 9/1985 | Howard | 359/819 |
| 4,564,736 | 1/1986 | Jones | 219/121 L |
| 4,917,083 | 4/1990 | Harrington | 606/15 |
| 4,979,180 | 12/1990 | Muncheryan | 372/92 |
| 5,074,861 | 12/1991 | Schneider | 606/17 |
| 5,125,923 | 6/1992 | Tanner | 606/10 |
| 5,200,604 | 4/1993 | Rudko | 250/205 |
| 5,262,900 | 11/1993 | Gerber | 359/811 |
| 5,291,336 | 3/1994 | Miles | 359/808 |
| 5,346,489 | 9/1994 | Levy | 606/15 |
| 5,464,436 | 11/1995 | Smith | 606/89 |

*Primary Examiner*—Georgia Y. Epps
*Assistant Examiner*—Ricky Mack
*Attorney, Agent, or Firm*—Iandiorio & Teska

[57] ABSTRACT

A non-reusable lens cell for a surgical laser handpiece having a contact surface with an aperture for exiting a laser beam includes a housing having a first connector at a first end for engaging a laser source and a second connector at a second end for engaging a handpiece; and a hydroscopic lens device for focusing the laser beam through the handpiece proximate the aperture and being degradable in the presence of moisture during attempts at sterilization to deteriorate the lens device, disrupt the focus and thwart reuse of the lens cell.

8 Claims, 2 Drawing Sheets

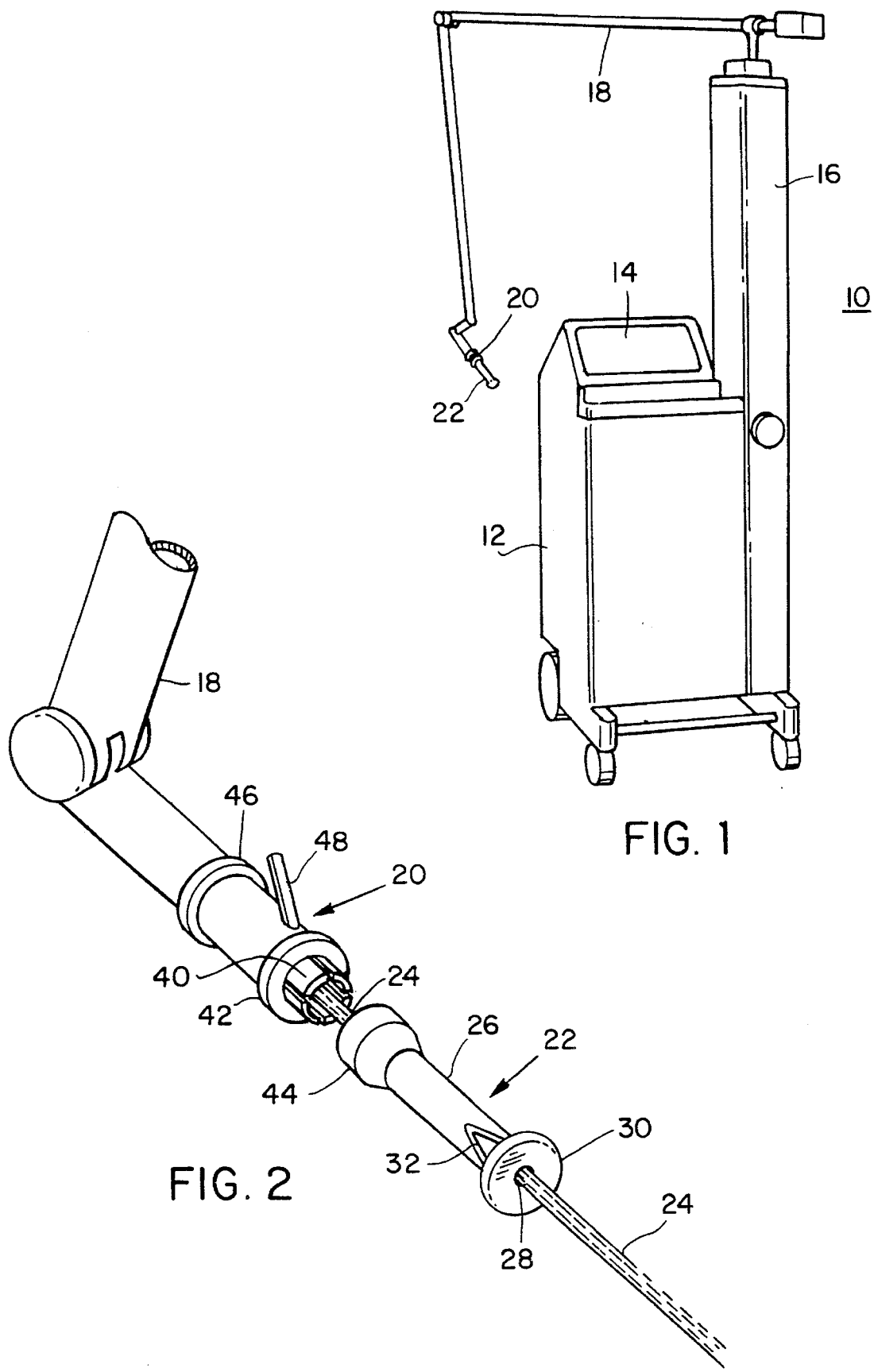

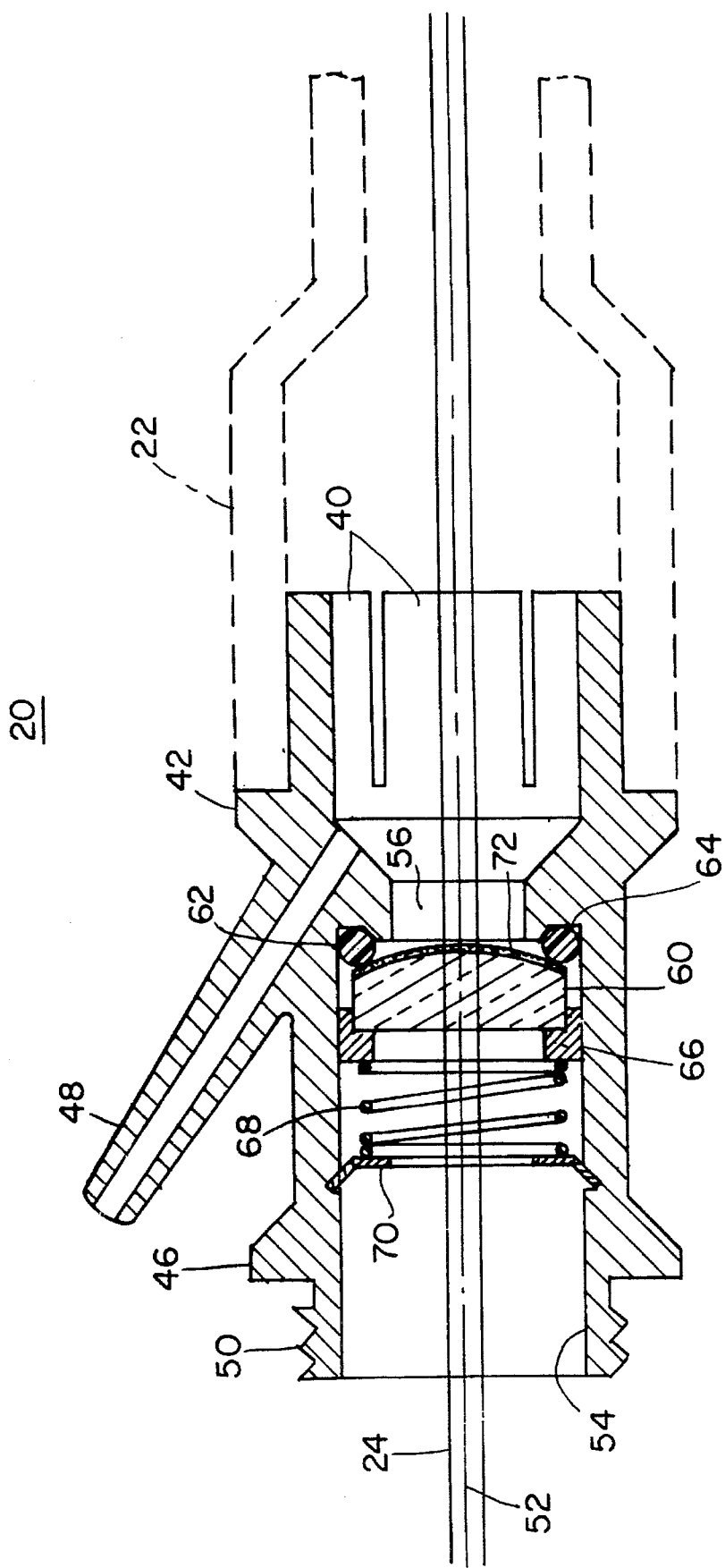

NON-REUSABLE LENS CELL FOR A SURGICAL LASER HANDPIECE

FIELD OF INVENTION

This invention relates to a non-reusable lens cell for a surgical laser handpiece which thwarts attempts to reuse a damaged or degraded lens by rendering it inoperable.

BACKGROUND OF INVENTION

Surgical lasers such as lasers used for transmyocardial revascularization (TMR) must provide accurate repeatable performance in order to insure proper safe operation on a beating human heart. Typically a $CO_2$ laser is used to generate a laser beam which is propagated through an articulated arm and a lens cell to a handpiece manipulated by the surgeon to direct the beam at the proper time, place and power to strike a hole in the heart wall precisely and safely. The handpiece generally has a contact surface at its distal end for contacting the beating heart and an aperture in that surface to allow the laser beam to exit and strike the heart wall. The lens cell contains a lens which focuses the laser beam near, at or beyond the contact surface so as to concentrate the beam energy at the desired site on the heart wall. A window in the handpiece above the contact surface provides a path for the ablative issue of the heart to pass out without contaminating the remainder of the handpiece, the lens cell and other components and optics upstream of it. Nevertheless, some steam, smoke and debris inevitably do find their way to the handpiece and lens cell and contaminate them and impair their optical efficiency.

To overcome this the parts are cleaned and sterilized after each use. However, it has been observed that the cleaning or sterilization itself can damage and degrade the lens in the lens cell. Typically these lenses are made of zinc selenide (ZnSe) which is highly corroded by the sterilizing, cleaning medium ethylene oxide (EtO). The EtO is generally applied over a three-hour period at 100% humidity and 130° C. temperature which seriously deteriorates among other things the anti-reflective coating on the lens. Without the coating as much as 15% of the light can be reflected back to the laser causing heating and damage. More importantly, the beam incident at the patient's heart will contain 15% less energy than the surgeon has called for and expects.

Also during the cleaning process encrusted blood, body fluids or tissue may require a nurse or attendant to physically remove the debris such as by rubbing or scraping, which can seriously damage the lens so that its focus is shifted or it is without focus, or the transmission properties can be otherwise interfered with or impaired.

SUMMARY OF INVENTION

It is therefore an object of this invention to provide an improved non-reusable lens cell for use with a handpiece on a surgical laser system.

It is a further object of this invention to provide such a lens cell which avoids the problems associated with the reuse of a lens cell degraded by cleaning and sterilization.

It is a further object of this invention to provide such a lens cell which eliminates the marring and degrading of the lens and the possible consequent shift or loss of focus and obscuration.

It is a further object of this invention to provide such a lens cell which decomposes the lens so the lens cell and the handpiece and surgical laser system which the lens cell serves is non-functional.

The invention results from the realization that a truly effective lens cell which avoids the problems associated with the use of a lens degraded by sterilization and cleaning can be achieved by constructing the lens out of a hydroscopic medium (e.g., NaCl, KCl) which decomposes in the sterilization and cleaning process rendering the lens cell wholly inoperable.

This invention features a non-reusable lens cell for a surgical laser handpiece having a contact surface with an aperture for exiting a laser beam. There is a housing having a first connector at a first end for engaging a laser source and a second connector at a second end for engaging a handpiece. A hydroscopic lens device focuses the laser beam through the handpiece proximate the aperture and is degradable in the presence of moisture during attempts at sterilization to deteriorate the lens device, disrupt the focus and thwart reuse of the lens cell.

In a preferred embodiment, the lens device may be formed from sodium chloride or from potassium chloride. The housing may include a chamber for receiving the lens device. The chamber may include a lens mounted on one side of the lens device and a seal on the other. The chamber may also include a fastener spaced from the lens mount and a spring between the fastener and lens mount for urging the lens mount against the lens device, the lens device against the seal and the seal against the chamber to snugly seal out ablative emissions from the handpiece. The lens device may be coated to protect it from ambient moisture. The coating may be an antireflective moisture resitant coating.

BRIEF DESCRIPTION OF THE DRAWINGS

Other objects, features and advantages will occur to those skilled in the art from the following description of a preferred embodiment and the accompanying drawings, in which:

FIG. 1 is a three-dimensional view of a surgical laser utilizing the lens cell according to this invention;

FIG. 2 is an enlarged exploded three-dimensional view of the lens cell of this device coupled between the end of the articulated arm and the handpiece of FIG. 1; and FIG. 3 is an enlarged detailed cross-sectional view of the lens cell according to this invention.

DISCLOSURE OF PREFERRED EMBODIMENT

The invention may be accomplished by constructing a non-reusable lens cell for a surgical laser handpiece, which handpiece has a contact surface with an aperture for exiting a laser beam. There is a housing with a first connector at one end for engaging a laser source and a second connector at the other end for engaging the handpiece. A hydroscopic lens device focuses the laser beam through the handpiece proximate the aperture. The hydroscopic lens device is degradable in the presence of moisture during attempts at sterilization to deteriorate the lens device, disrupt the focus and thwart reuse of the lens cell. The lens device may be formed of any transparent hydroscopic material such as sodium chloride which decomposes readily in the presence of moisture. The housing typically includes a chamber for receiving the lens device. The lens device may be coated to protect it from ambient moisture during its normal operation, to allow the distal surface to be wiped with a damp swab and to reduce reflections from the surface of the substrate. Such a coating may be an antireflective, moisture resistant coating such as magnesium fluoride or thorium fluoride. The lens device is sealed against the end toward the handpiece in order to prevent ablative smoke and steam produced by the impact of the laser heat on the human tissue from reaching and clouding or contaminating the lens. There is a seal between the lens and the end of the chamber toward the handpiece. On the other side of the lens is a lens mount with a spring and some securing means to insure that the spring urges the lens mount against the lens, the lens against the seal and the seal against the chamber to complete the sealing process.

There is shown in FIG. 1 a surgical laser 10 which includes for example control and power circuits 12, a display monitor and control panel 14, a $CO_2$ laser 16, and articulated arm 18 that propagates the laser beam from laser 16 through lens call 20 to handpiece 22. Laser beam 24, FIG. 2, passes through barrel 26 of handpiece 22 and exits through aperture 28 in contact surface 30. Window 32 is provided to allow ablative plumes caused by the heating of the human tissue by the laser beam to minimize contamination of handpiece 22 and lens cell 20. Lens cell 20 includes tensioned fingers 40 which extend from shoulder 42 to slip fit with the inside of collar 44 of handpiece 22. A similar shoulder 46 is disposed on the side of lens cell 20 toward articulated arm 18. A pipe or nipple 48 extends radially outward to allow purge gas to be introduced into lens cell 20 ahead of the lens to purge it and keep it clean from contaminants.

Threads 50, FIG. 3, at the other end connect lens cell 20 to the end of articulated arm 18. Laser beam 24, centered on the center line axis 52 of lens cell 20, passes right through annular chamber 54 and opening 56 into the area encompassed by tension fingers 40. Lens 60 in chamber 54 is shown as a planar convex lens which may be formed of a suitable transparent hydroscopic material such as sodium chloride or potassium chloride. An O-ring gasket 62 provides a seal between the convex portion of lens 60 and the annular recess 64 of chamber 54. Lens mounting 66 is urged against the planar side of lens device 60 by spring 68 which is held in position by a fastener such as star ring 70. A coating 72 is provided on lens device 60 to retard moisture penetration so that during normal shipping, shelf life, and use lens device 60 is not degraded but that during cleaning and sterilization process where elevated humidities and temperatures prevail, the coating will deteriorate and the lens will decompose so that the lens cell is totally non-functional and the laser beam will not be focused and cannot accomplish its intended purpose: the lens cell must be replaced. Pipe 48 is provided as a means to introduce a purging fluid such as nitrogen or another inert gas which clears debris, smoke and steam from holes 56 and the area within tension fingers 40 to keep lens device 60 clear during use. The purging fluid along with the contaminants exits window 32, FIG. 2. Since the lens cell must be sterilized and since the humidity associated with sterilization causes the lens device to decompose, the lens cell cannot be reused. Any attempt to clean it or sterilize it as is necessary will decompose the lens device to make the lens cell ineffectual and inoperable. Thus the surgeon and the patient are assured that only clean, sterile and wholly safe and operable lens cells can be used.

Lens cell 20 is sterilized initially before its first and only use, using techniques which do not employ EtO or other substances that will decompose or degrade the lens device, for example, cobalt issued gamma ray sterilization.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A non-reusable lens cell for a surgical laser handpiece having a contact surface with an aperture for exiting a laser beam, comprising:

a housing having a first connector at a first end for engaging a laser source and a second connector at a second end for engaging a handpiece; and a hydroscopic lens device for focusing the laser beam through the handpiece proximate the aperture and being degradable in the presence of moisture during sterilization to deteriorate the lens device, disrupt the focus and thwart reuse of the lens cell.

2. The non-reusable lens cell of claim 1 in which said lens device is formed of NaCl.

3. The non-reusable lens cell of claim 1 in which said lens device is formed of KCl.

4. The non-reusable lens cell of claim 1 in which said housing includes a chamber for receiving said lens device.

5. The non-reusable lens cell of claim 4 in which said chamber includes a lens mount on one side of said lens device and a seal on the other.

6. The non-reusable lens cell of claim 5 in which said chamber includes a fastener spaced from said lens mount and a spring between said fastener and lens mount for urging said lens mount against said lens device, said lens device against said seal and said seal against said chamber to snugly seal out ablative emissions from the handpiece.

7. The non-reusable lens cell of claim 1 in which said lens device is coated to protect it from ambient moisture.

8. The non-reusable lens cell of claim 1 in which said lens coating is an antireflective moisture resistant coating.

* * * * *